(12) United States Patent
Bottomley

(10) Patent No.: US 10,912,902 B2
(45) Date of Patent: Feb. 9, 2021

(54) DISPENSING APPARATUS

(71) Applicant: Nasaleze Patents Ltd, Isle of Man (GB)

(72) Inventor: Simon Bottomley, Isle of Man (GB)

(73) Assignee: Nasaleze Patents Limited

( * ) Notice: Subject to any disclaimer, the term of this patent is extended or adjusted under 35 U.S.C. 154(b) by 0 days.

(21) Appl. No.: 15/504,220

(22) PCT Filed: Aug. 18, 2015

(86) PCT No.: PCT/GB2015/052392
§ 371 (c)(1),
(2) Date: Feb. 15, 2017

(87) PCT Pub. No.: WO2016/027075
PCT Pub. Date: Feb. 25, 2016

(65) Prior Publication Data
US 2017/0232213 A1     Aug. 17, 2017

(30) Foreign Application Priority Data

Aug. 20, 2014   (GB) .................................. 1414796.1

(51) Int. Cl.
*A61M 15/00*     (2006.01)
*G01F 11/26*     (2006.01)
(Continued)

(52) U.S. Cl.
CPC ...... *A61M 15/0065* (2013.01); *A61M 11/008* (2014.02); *B65D 1/32* (2013.01);
(Continued)

(58) Field of Classification Search
CPC ............ A61M 11/008; A61M 15/0065; A61M 2202/064; B65D 41/04; B65D 1/32;
(Continued)

(56) References Cited

U.S. PATENT DOCUMENTS 1,687,705 A * 10/1928 Lambro ................ G01F 11/263
222/424
1,941,745 A * 1/1934 Higley .................. G01F 11/261
222/456
(Continued)

FOREIGN PATENT DOCUMENTS

WO    2013167715    11/2013
WO    2016027075    2/2016

OTHER PUBLICATIONS

PCT/GB2015/052392 International Search Report dated Aug. 18, 2015.
(Continued)

*Primary Examiner* — Paul R Durand
*Assistant Examiner* — Robert K Nichols, II
(74) *Attorney, Agent, or Firm* — Nyemaster Goode, PC

(57) ABSTRACT

Dispensing apparatus is provided for delivering and/or dispensing a pre-determined amount of a product in use. The apparatus includes dispensing mechanism having an inlet for allowing product to enter the dispensing mechanism in use, an outlet for allowing product containable within the dispensing mechanism in use to be dispensed therefrom during a dispensing action of the apparatus, and a channel provided between the inlet and the outlet for allowing product to move between the inlet and the outlet in use.

10 Claims, 5 Drawing Sheets

(51) Int. Cl.
*A61M 11/00* (2006.01)
*G01F 15/00* (2006.01)
*B65D 1/32* (2006.01)
*B65D 41/04* (2006.01)
*B65D 83/06* (2006.01)

(52) U.S. Cl.
CPC ............ *B65D 41/04* (2013.01); *B65D 83/06* (2013.01); *G01F 11/261* (2013.01); *G01F 15/007* (2013.01); *A61M 2202/064* (2013.01)

(58) Field of Classification Search
CPC ..... B65D 83/06; B65D 47/123; G01F 11/261; B05B 11/0059
USPC ................. 222/456, 207, 211, 546, 420–422
See application file for complete search history.

(56) References Cited

U.S. PATENT DOCUMENTS

| | | | | |
|---|---|---|---|---|
| 2,718,987 A * | 9/1955 | Kimball | ................ | B05B 11/041 222/207 |
| 2,989,215 A * | 6/1961 | Willingham | .............. | B05B 7/24 222/207 |
| 3,146,919 A * | 9/1964 | Chappell | ............... | G01F 11/265 222/212 |
| 3,241,726 A * | 3/1966 | Chester | .............. | B65D 47/2031 222/211 |
| 4,356,941 A * | 11/1982 | McRoskey | .......... | B05B 11/0059 222/211 |
| 4,438,869 A * | 3/1984 | Vierkotter | ............ | G01F 11/265 222/1 |
| 4,579,858 A | 4/1986 | Ferno | | |
| 4,756,433 A * | 7/1988 | Lin | ........................ | B65D 23/00 215/307 |
| 4,830,226 A * | 5/1989 | Kong | ................... | B67D 7/0216 222/207 |
| 5,346,105 A | 9/1994 | Onneweer | | |
| 5,865,353 A * | 2/1999 | Baudin | ............. | B65D 47/0814 215/235 |
| 5,971,234 A * | 10/1999 | Mathison | .............. | B05B 11/045 222/211 |
| 6,076,709 A * | 6/2000 | Wilner | ................... | B65D 47/18 222/212 |
| 6,089,411 A * | 7/2000 | Baudin | ............. | B65D 47/2031 222/212 |
| 6,276,572 B1 * | 8/2001 | Evans | .................... | B65D 1/023 222/424.5 |
| 2003/0160068 A1 * | 8/2003 | Mehta | .................... | A61H 35/04 222/211 |
| 2004/0082907 A1 * | 4/2004 | James | .................... | A45D 33/02 604/58 |
| 2010/0108062 A1 * | 5/2010 | Ganem | ............. | A61M 15/0028 128/203.21 |
| 2015/0217895 A1 * | 8/2015 | Romanov | ............. | B65D 1/323 222/464.1 |

OTHER PUBLICATIONS

PCT/GB2015/052392 Written Opinion of the International Searching Authority.

* cited by examiner

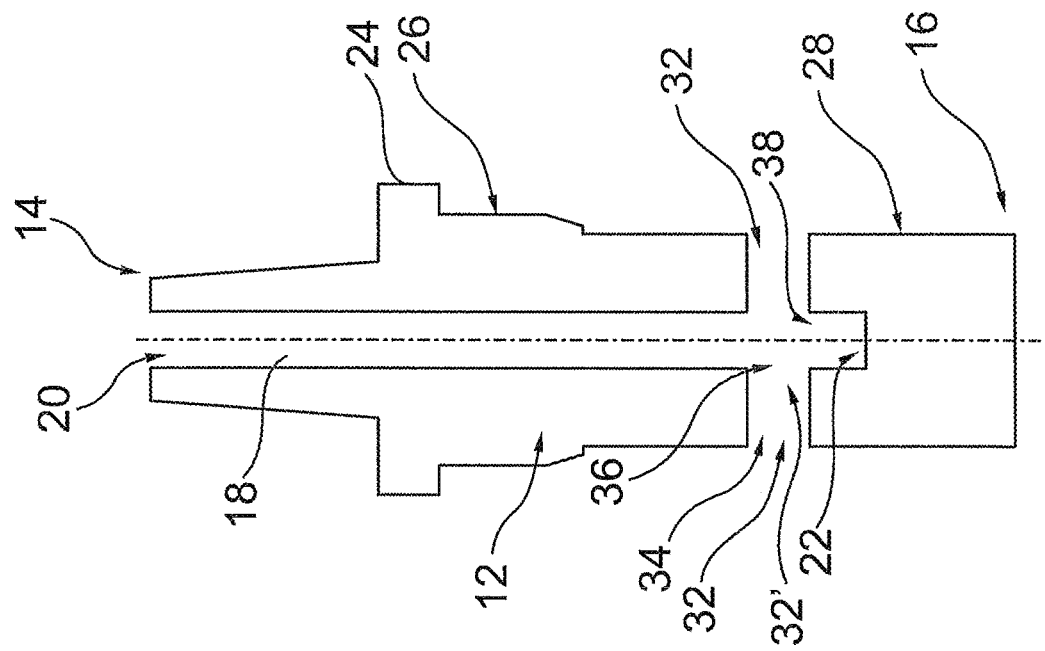
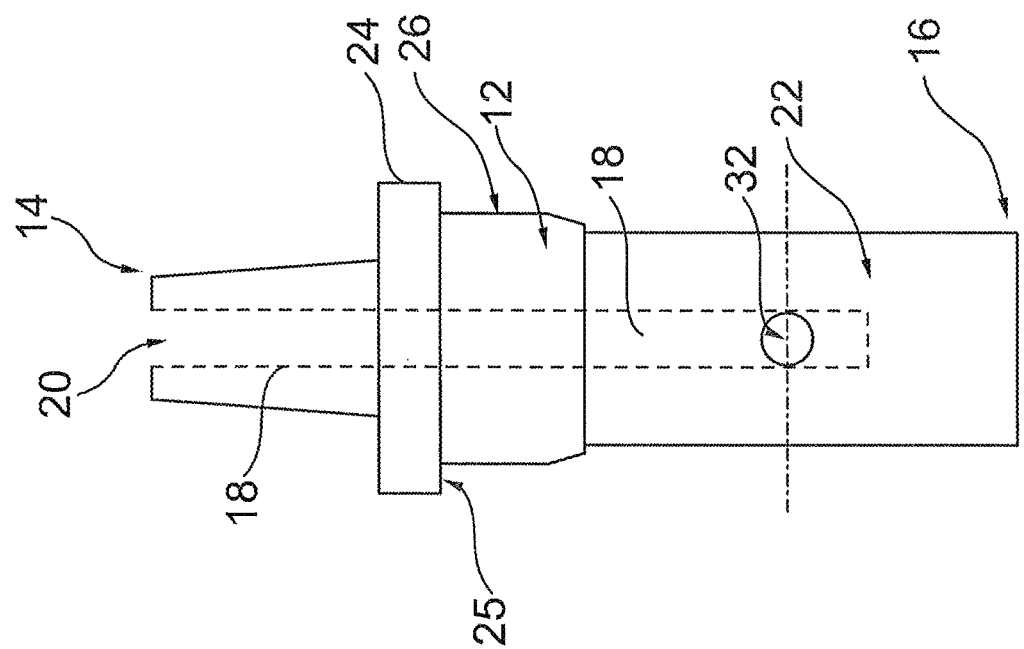

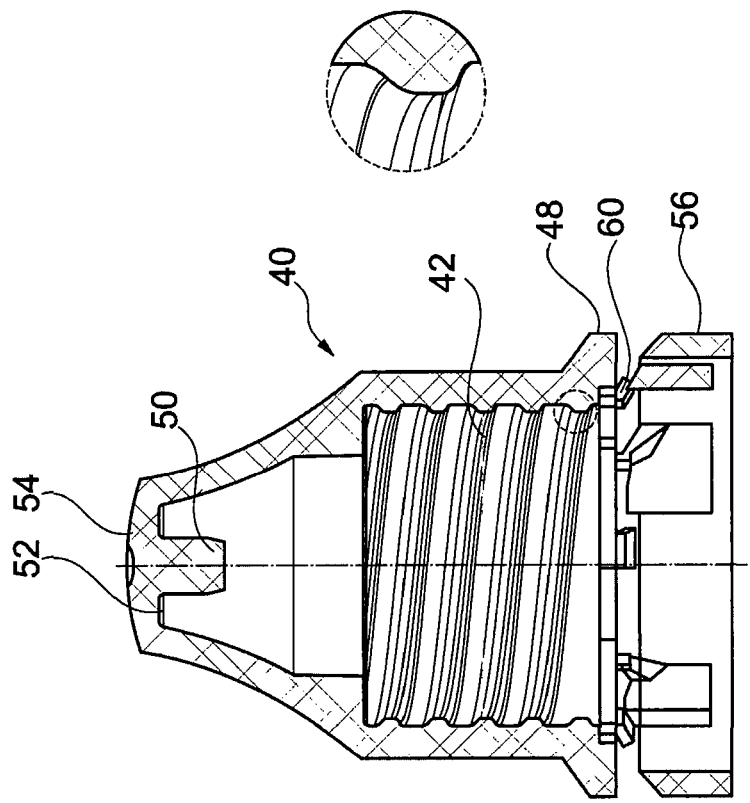
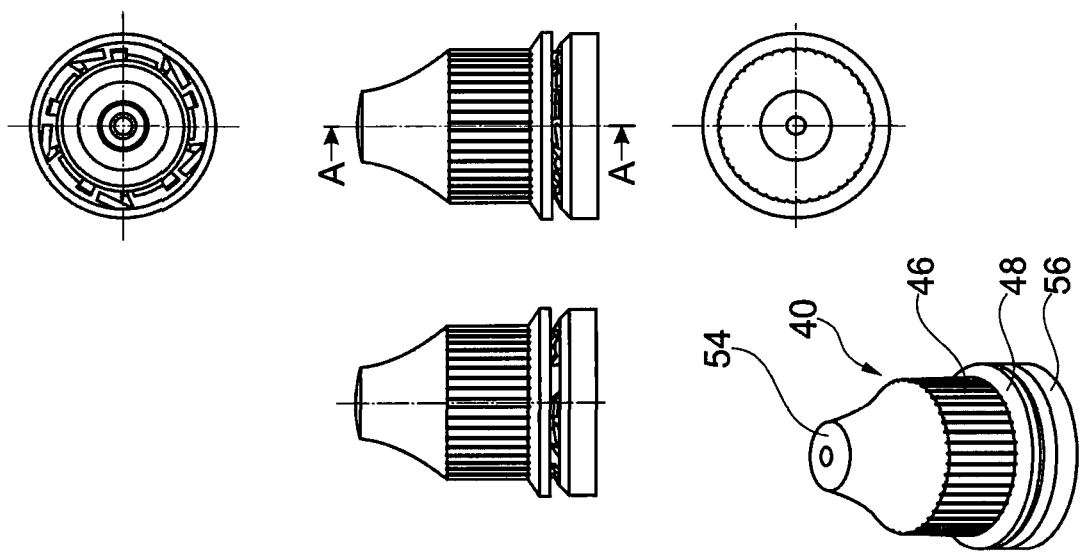
Fig. 3b
Fig. 3a 800 mg Bottle Testing for amount of doses in 15 ml bottle
M&H 15 ML BOTTLE WITH A METERED DOSE PEG WITH 800 MG OF HPMC AND MINT

| Bottle Number | Bottle weight before application | No. of doses | Bottle weight after application | Amount used in grams | Average weight of power per application |
|---|---|---|---|---|---|
| 1 | 6.7 g | 201 | 5.9 g | 0.8 g | 0.0039801 |
| 2 | 6.8 g | 204 | 6 g | 0.8 g | 0.003921569 |
| 3 | 6.7 g | 202 | 5.9 g | 0.8 g | 0.003960396 |
| 4 | 6.8 g | 201 | 6 g | 0.8 g | 0.0039801 |
| 5 | 6.8 g | 200 | 6 g | 0.8 g | 0.004 |
| 6 | 6.8 g | 201 | 5.9 g | 0.9 g | 0.004477612 |
| 7 | 6.8 g | 202 | 6 g | 0.8 g | 0.003960396 |
| 8 | 6.7 g | 200 | 5.9 g | 0.8 g | 0.004 |
| 9 | 6.8 g | 203 | 6 g | 0.8 g | 0.003940887 |
| 10 | 6.8 g | 201 | 6 g | 0.8 g | 0.0039801 |
| Averages | 6.77 g | 201.5 | 5.96 g | 0.81 g | 0.004020116 |

Fig. 4

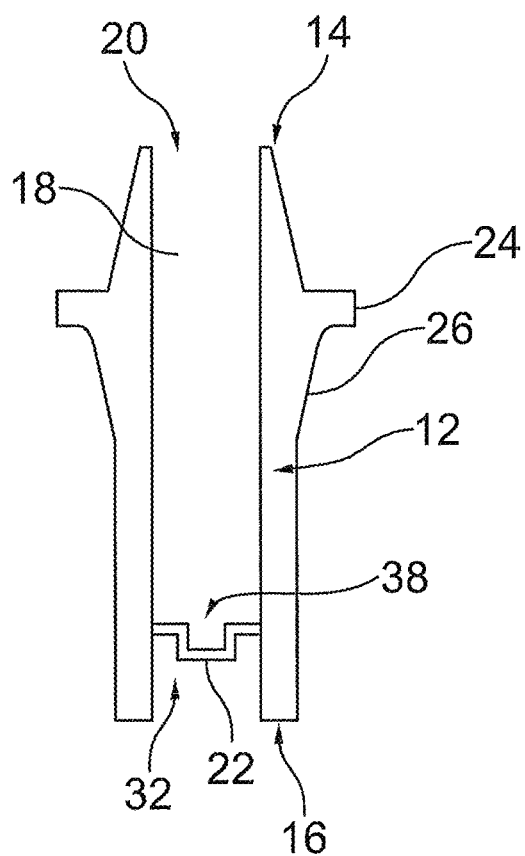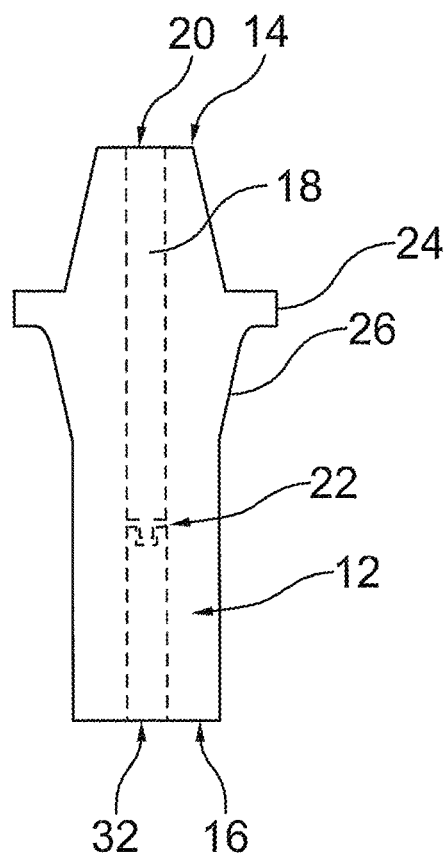
Fig. 5a          Fig. 5b
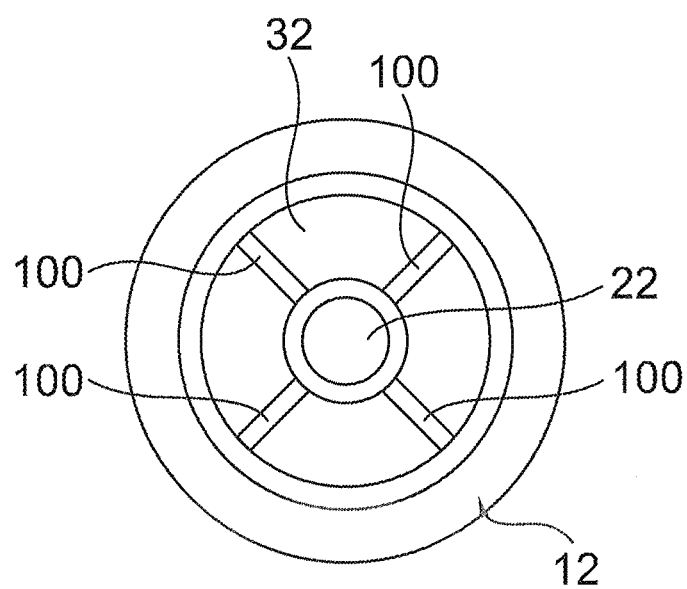
Fig. 5c

DISPENSING APPARATUS

This invention relates to dispensing apparatus and to a method of use thereof.

Although the following description refers almost exclusively to metered dose dispensing apparatus for delivering and/or dispensing a pre-determined amount of a powdered composition to the nasal cavity of a human or animal, it will be appreciated by persons skilled in the art that the dispensing apparatus could be used to delivery and/or dispense a pre-determined amount of any product, be it a liquid, fluid and/or powder to the nasal cavity, oral cavity and/or any other suitable location as required.

The applicants have a granted patent EP1368090 for apparatus for dispensing powdered material therefrom in a manner that regulates, to an extent, the amount of powder delivered therefrom. The apparatus comprises a deformable bottle providing a repository for powdered material. The bottle has an outlet and a conduit is provided in the bottle that extends between the outlet and the base of the bottle. A volume of air can be propelled through the powdered material resting in the repository by squeezing the sides of the bottle. The propelled air entrains the powdered material and carries the powdered material along the conduit and out through the outlet. A restrictive notch is provided adjacent the base of the conduit and this notch restricts the amount of entrained powder that can enter the conduit compared to the amount of powder that would be able to enter the conduit in the absence of the restrictive notch. This restriction thereby regulates the amount of powder delivered by the apparatus. However, a problem with this apparatus is that the regulation of the amount of powder delivered by the apparatus is not sufficiently accurate and reproducible for each dispensing action.

It is therefore an aim of the present invention to provide dispensing apparatus wherein a pre-determined amount of a product, or metered dosage can be accurately and reproducibly delivered and/or dispensed via the same.

It is a further aim of the present invention to provide a method of using dispensing apparatus.

According to a first aspect of the present invention there is provided dispensing apparatus for delivering and/or dispensing a pre-determined amount of a product in use, said apparatus including dispensing means having inlet means for allowing product to enter the dispensing means in use, outlet means for allowing product containable within the dispensing means in use to be dispensed therefrom during a dispensing action of the apparatus, and channel means provided between the inlet means and the outlet means for allowing product to move between the inlet means and the outlet means in use, and wherein recess means are defined in the channel means, dimensions of the recess means defining or substantially defining the pre-determined amount of product that can be delivered through the outlet means for each dispensing action of the apparatus, and wherein the inlet means and/or at least one aperture defined in the dispensing means is arranged and/or is of such dimensions that excess product contained in the channel means that cannot fit into the recess means is able to pass through said inlet means and/or said at least one aperture and out of the channel means in use prior to a dispensing action of product from the outlet means.

Thus, the dispensing apparatus of the present invention can act as metered dose dispensing apparatus in that it can deliver a pre-determined amount or a metered dose of a product, material or composition in use. The size or volume of the recess means typically defines the metered dose or volume that can be delivered via the dispensing apparatus in any single dispensing action.

Preferably a dispensing action of the dispensing apparatus includes the steps of product entering the channel means of the dispensing means via the inlet means and/or the at least one aperture, product contained within the channel means entering the recess means, excess product not fitting into the recess means passing back through the inlet means and/or through the at least one aperture of the dispensing means so that the channel means is clear or substantially clear of product, at least just prior to dispensing the product contained within the recess means through the outlet means of the dispensing means.

The channel means is typically defined in the dispensing means or the dispensing means consists of or includes the channel means. For example, the channel means could be in the form of a channel member, sleeve member, product flow pathway, any hollow body in which a product can flow or move through in use and/or the like.

Preferably the inlet means and/or the outlet means is in the form of or includes one or more apertures. The one or more apertures are typically defined in the dispensing means and/or channel means.

Preferably the inlet means and/or at least one aperture is arranged in at least one wall of the channel means in such a position or positions that substantially only the product contained in the recess means is delivered per dispensing action of the apparatus. Any remaining product that may be present in the channel means but not located in the recess means is arranged to pass through the inlet means and/or at least one further aperture and out of the channel means prior to dispensing of the product through the outlet means takes place.

Preferably a channel is defined in the channel means. The channel acts as a flow pathway for the product in use.

Preferably the recess means is defined in a wall or walls of the channel means that defines the channel. The recess means provides at least one recess or compartment with respect to the main channel of the channel means and is arranged so as to allow product to be retained therein during a pre-dispensing action or a dispensing action.

In one embodiment the recess means is set back or recessed with respect to the main channel of the channel means.

In one embodiment the inlet means and/or the at least one aperture is defined in the channel means a pre-determined spaced distance apart from the recess means.

Preferably the inlet means and/or the at least one aperture is located between the recess means and the outlet means, and further preferably is located above the recess means when the dispensing apparatus is in a first upright position.

In one embodiment the recess means is located a spaced distance between the outlet means and the inlet means and/or the at least one aperture.

In one embodiment the inlet means and/or the at least one aperture is defined in the channel means below the recess means, when the dispensing apparatus is in a first upright position. In this arrangement the outlet means and the recess means is typically above and vertically spaced from the inlet means and/or at least one aperture.

Preferably the first upright position corresponds to when the dispensing apparatus is in a non-use or pre-primed position.

Preferably the outlet means are provided at or adjacent a first end of the channel means.

In one embodiment the inlet means and/or the at least one aperture is defined in an end wall of the channel means. Preferably the inlet means and/or the at least one aperture is defined in a second end of the channel means, and further preferably the second end is opposite to the first end.

In one embodiment the inlet means and/or the at least one aperture is arranged on a side wall of the channel means. Preferably the side wall is provided between first and second ends of the channel means.

Preferably the inlet means and/or the at least one aperture is arranged transverse to the outlet means. For example, a central axis taken through the inlet means and/or the at least one aperture is arranged transverse, perpendicular or substantially perpendicular to a central axis taken through the outlet means.

In one embodiment the recess means is provided at or adjacent a second end of the channel means.

Preferably the second end of the channel means in which the recess means is located in, adjacent to, or at is a blind end.

In one embodiment the inlet means, the at least one aperture and/or one or more walls defining the inlet means and/or the at least one aperture have a narrowing taper from an external wall of the channel means to an internal wall of the channel means and/or vice versa so as to allow product to more easily pass into and/or out of the inlet means and/or aperture in use.

In one embodiment the inlet means, the at least one aperture and/or the one or more walls defining the inlet means and/or at least one aperture are linear in form, substantially linear in form or are non-tapered in form from an external wall of the dispensing means or channel means to an internal wall of the dispensing means or channel means.

In one embodiment two or more inlet means and/or apertures are defined in the channel means. The two or more inlet means and/or apertures can be of substantially the same shape and/or dimensions or can be of different or substantially different shapes and/or dimensions to each other.

In one embodiment the two or more inlet means and/or apertures can be located at the same or substantially the same height, and/or distance from the first and/or second ends of the channel means. Alternatively the inlet means and/or the two or more apertures can be located at different or substantially different heights and/or distances from or with respect to the first and/or second ends of the channel means.

The two or more inlet means and/or apertures can be arranged to be opposite or substantially opposite to each other or the two or more inlet means and/or apertures can be arranged not to be opposite each other.

In one embodiment the recess means is suspended and/or supported within the channel means at a suitable location and one or more further apertures or spaces are defined wholly or partially around the recess means to allow excess product not contained within the recess means to move past the recess means in use.

Preferably product flowing past the recess means passes out through a second end, inlet means and/or one or more apertures defined below the recess means and/or between the recess means and a second end of the channel means.

In one embodiment one or more arms are provided to support and/or suspend the recess means within the channel means. The one or more arms are typically located between an internal wall of the channel means and an external wall of the recess means.

Preferably at least one aperture is defined in the outlet means to allow product contained within the recess means to pass therethrough during a dispensing action or on completion of a dispensing action.

The recess means can be any recess, reservoir, compartment, sub-compartment, cup like member and/or the like that can hold a pre-determined amount of product therein in use.

The recess means can be attached to the channel means or can be integrally formed therewith.

Preferably the dispensing apparatus includes a deformable and/or flexible bottle, container or reservoir into which the dispensing means and/or channel means is/are located in use.

Preferably deformation or flexing of the bottle, container or reservoir such as for example, as a result of a user squeezing one or more sides of the bottle, allows a volume of air or gas containable within the bottle, container or reservoir to be propelled through the inlet means and/or at least one aperture in the channel means, along the channel means, and out through the outlet means of the dispensing means. As the propelled air or gas passes the recess means in the channel means, it carries or entrains the product contained within the recess means with it and out through the outlet means. This action is typically a dispensing action.

Squeezing the sides of the deformable bottle, container or reservoir, such as for example by a user using their fingers, typically increases the internal pressure of the bottle when compared to atmospheric pressure resulting in an airflow that is channelled out of the bottle through the outlet means.

Preferably the bottle, container or reservoir is formed such that with the channel means and/or dispensing means located in or fitted to the same in use, a product contained within the bottle, container or reservoir can only be dispensed via the outlet means of the channel means in use.

Preferably the amount of product located in the bottle, container or reservoir is such that it sits or rests below the level of the inlet means and/or at least one aperture of the channel member when the bottle, container or reservoir is in an upright or storage position. This allows air or gas contained within the bottle, container or reservoir to easily pass into and out of the inlet means and/or at least one aperture. It also allows excess composition to pass into and out of the inlet means and/or at least one aperture without obstruction.

In one embodiment the channel means is integrally formed with the bottle, container or reservoir.

In one embodiment the bottle, container or reservoir has an opening and the dispensing means and/or channel means is located in or fitted in the opening in use.

The channel means and/or dispensing means can located in or be fitted in the opening of the bottle, container or reservoir by friction fit, interference fit, snap-fit and/or via attachment means, such as for example using a screw thread arrangement, using a protrusion/recess arrangement, snap-fit connection, welding, adhesive, inter-engaging members and/or the like.

In one embodiment the dispensing apparatus has to be primed prior to a dispensing action taking place to allow product contained within the bottle, container or reservoir to be moved from the bottle, container or reservoir, into the dispensing means and into the recess means of the channel means.

Preferably priming of the dispensing apparatus involves inverting the bottle, container or reservoir such that product contained within the bottle, container or reservoir can pass through the inlet means and/or at least aperture defined in the dispensing means and/or channel means and into the channel means. Once the bottle, container or reservoir is returned to an upright or starting position, some product falls into the recess means within the channel means and the remaining product that cannot fit into the recess means passes through the inlet means and/or at least one aperture of the channel means and back into the bottle, container or reservoir. The bottle, container or reservoir is then flexed or deformed to perform a dispensing action with the bottle, container or reservoir in the upright or starting position.

Preferably the outlet means is located at a top of a bottle, container or reservoir and inverting the bottle, container or reservoir during priming moves a base of the bottle, container or reservoir above the outlet means, thereby allowing product contained within the bottle, container or reservoir to move under gravity into the dispensing means and/or channel means.

Preferably the bottle, container or reservoir may need to be tapped against a surface and/or shaken one or more times during the priming action to help move product contained therein into the channel means, the recess means and/or out of the channel means as required.

In one embodiment a cap, lid or closure means can be provided over the outlet means of the dispensing means and/or channel means when in the bottle, container or reservoir to prevent product passing therethrough during the priming process, or when the apparatus is not in use.

Preferably a pin or protrusion member defined on an interior surface of the cap, lid or closure means locates in an aperture of the outlet means when said cap, lid or closure means is engaged on or located with the outlet means in use.

Preferably the deformable and/or flexible bottle, container or reservoir is formed from approximately, equal to, or at least 90% LDPE (low density polyethylene) and approximately, equal to, or less than 10% HDPE (high density polyethylene).

In one embodiment the deformable and/or flexible bottle, container or reservoir is formed from approximately or equal to 100% LDP (low density polyethylene).

Preferably the deformable and/or flexible bottle, container or reservoir has sufficient deformity and/or flexion to allow a sufficient change in air or gas pressure within the interior of the bottle, container or reservoir to allow a product located in the recess means to be entrained in the air or gas as it passes through the channel means.

Preferably the bottle, container or reservoir can contain any amount of product to provide a dosage of 0.001 mg to 20 mg.

Preferably the volume of the bottle, container or reservoir is such so as to contain 5-50 mm of liquid.

Preferably the dimensions of the inlet means and/or at least one aperture are approximately 0.1-8 mm in diameter in order to prevent blocking of the same in use.

In one embodiment the inlet means and/or at least one aperture is located between 0-12 mm from a first end or outlet means of the dispensing means and/or channel means.

Preferably the diameter of the channel defined within the dispensing means and/or channel means is approximately or equal to 2.5 mm so as to prevent blocking of the same in use.

The dispensing means and/or channel means can be made from any or any combination of suitable materials, such as for example, plastic, metal, rubber, wood and/or the like. In a preferred example the dispensing means and/or channel means is made from a plastic material. The plastic material can have a gloss finish or can have an etched finish as required.

The dispensing apparatus can be used on a human or animal as required.

Preferably the apparatus is used for delivering product to a nasal cavity of a human or animal.

In one embodiment the product being dispensed and/or the product contained within the bottle, container or reservoir is a powder.

Preferably the powdered material includes or contains a cellulose based material, such as for example hydroxypropylmethylcellulose (HPMC) and/or the like.

In one embodiment the product being dispensed and/or the product contained within the bottle, container or reservoir is a liquid.

In one embodiment any or any combination of one or more suitable active agents, drugs, pharmaceuticals, additives, herbal agents and/or the like can be provided in the product, composition, liquid as required.

According to a second aspect of the present invention there is provided a method of using dispensing apparatus for delivering and/or dispensing a pre-determined amount of a product in use, said apparatus including dispensing means having inlet means for allowing product to enter the dispensing means in use, outlet means for allowing product containable within the dispensing means in use to be dispensed therefrom during a dispensing action of the apparatus, and channel means provided between the inlet means and the outlet means for allowing product to move between the inlet means and the outlet means in use, and wherein said method includes the steps of moving product through the inlet means and into the channel means of the dispensing means, allowing product contained within the channel means to move into recess means defined in the channel means, dimensions of the recess means defining or substantially defining the pre-determined amount of product that can be delivered through the outlet means for each dispensing action of the apparatus, allowing excess product contained in the channel means that cannot fit into the recess means to move through the inlet means and/or at least one aperture and out of the channel means prior to dispensing product contained within the recess means from the outlet means.

According to a third aspect of the present invention there is provided metered dose dispensing apparatus for delivering and/or dispensing a pre-determined amount of a composition, said apparatus comprising a channel member having outlet means for dispensing the pre-determined amount of composition therefrom in use and recess means defined in said channel member, dimensions of the recess means substantially defining the metered dose that can be delivered via the apparatus per dispensing action, and wherein at least one further aperture is defined in at least one wall of said channel member and is of such dimensions to allow excess composition that cannot fit in the recess means to pass therethrough in use prior to a dispensing action taking place.

According to a fourth aspect of the present invention there is provided a method of providing a metered dose using dispensing apparatus.

The apparatus of the present invention provides a metered dose to be accurately and reproducibly delivered each dispensing action, thereby preventing over dosing or under dosing of a composition.

Embodiments of the present invention will now be described with reference to the accompanying figures, wherein:

FIGS. 2a and 2b show an external view and a cross sectional view of a channel member forming part of the metered dose dispensing apparatus respectively according to an embodiment of the present invention;

FIGS. 3a and 3b show an external view and a cross sectional view of the lid for the dispensing bottle according to an embodiment of the present invention respectively;

FIG. 4 shows a table with experimental results illustrating the dispensing action accuracy of dispensing apparatus according to the present invention;

FIGS. 5a-5c show a cross sectional view, an external view and an end view from the outlet means end of the dispensing apparatus according to a further embodiment of the present invention respectively.

Figure 1A:
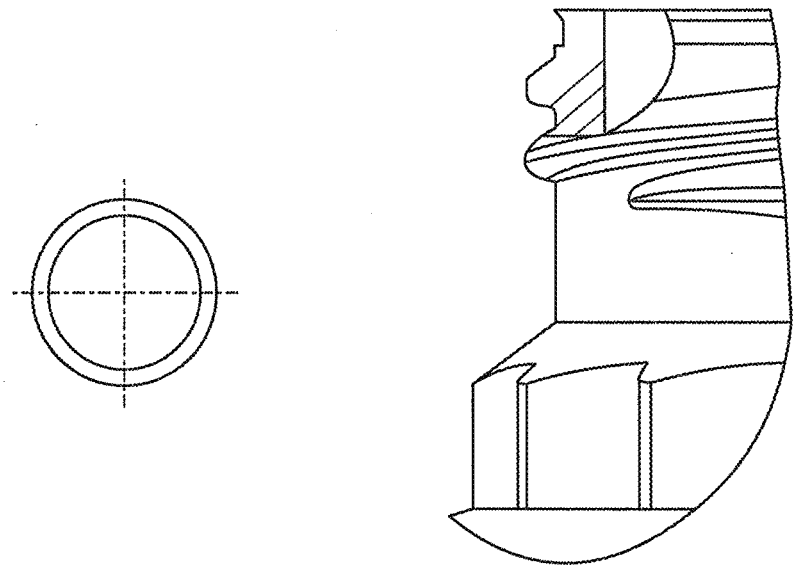
FIGS. 1a and 1b show metered dose dispensing apparatus with a lid fitted and the lid removed respectively according to one embodiment of the present invention.

Referring firstly to FIGS. 1a-3b, there is illustrated metered dose dispensing apparatus 2 according to an embodiment of the present invention comprising a deformable bottle 4. The bottle 4 has a base 6, a top 8 and side walls 10.

A channel member 12 is located in bottle 4. The channel member 12 is substantially elongate in form having outlet means provided at a first end 14 and a second blind, opposite end 16.

A hollow channel 18 is defined through channel member 12 between an outlet aperture 20 defined at first end 14 and a recess 22 defined adjacent second blind end 16. The recess 22 is of such dimensions and shape so as to contain a pre-determined amount of a composition. The hollow channel 18 in this example is linear in form.

Channel member 12 has an outwardly protruding flange 24 provided a spaced distance apart from first end 1. A lower surface 25 of flange 24 sits on the top surface 8 of bottle 4 in use. The outlet means has a narrowing taper from flange 24 towards first end 14 to allow the outlet means to be at least partially located in a cavity in which the composition is to be dispensed in use, such as for example, the nasal cavity of a human.

A section 26 of channel member 12 adjacent and below flange 24 is of slightly larger dimensions than a section 28 adjacent second end 16. The external dimensions of section 26 are slightly smaller than the internal dimensions of a neck section 30 of bottle 4 located below top surface 8 to allow a snug friction fit engagement between the channel member 12 and the bottle 4 in use.

A pair of further apertures 32 are defined in section 28 of channel member 12 above recess 22. The apertures 32 are in communication with hollow channel 18 and the bottle 4.

In the illustrated example, the apertures 32 are substantially of the same dimensions and shape and are located substantially opposite to each other in side walls of the channel member 12. The apertures 32 are shown as being substantially linear in form but could have a narrowing and/or broadening taper to allow composition to pass therethrough in a particular direction with greater ease if required.

Each further aperture 32 is typically in the form of a channel 32' having an opening 34 defined on an external surface of channel member 12 and an opening 36 defined on an internal surface of a wall defining hollow channel 18. The further aperture channel 32' is provided substantially perpendicular to hollow channel 18. The internal opening 36 of further aperture 32 is located directly above an opening 38 of recess 22. A wall of channel 32' is substantially level or flush with the opening 38 of recess 22. As such, any excess composition that is not located in recess 22 typically passes through further apertures 32 located either side of recess 22.

The recess 22 in the illustrations is located in line and co-axial with hollow channel 18.

Closure means in the form of a cap 40 is provided over top 8 of bottle 4 in use. In this example, the cap 40 is a screw cap having an internal threaded screw arrangement 42 for engagement with a complementary threaded screw arrangement 44 provided on an outer surface of neck section 30 of bottle 4 in use.

A plurality of rib members 46 are provided on an external surface of cap 40 adjacent a lower edge 48 thereof to allow easy gripping of the cap 40 by a user to rotate the cap into and out of engagement with the bottle 4 in use.

A pin 50 is located on an inner surface 52 of top 54 of cap 40 and protrudes inwardly and/or downwardly of top 54. With the cap 40 located on top 8 of bottle 4, the pin 50 locates in outlet aperture 20 of channel member 12, thereby preventing composition from exiting the channel member 12.

Tamper evident means 56 are provided on cap 40 that engage with a plurality of outwardly protruding ribs 58 on neck section 30 of bottle 4. In the illustrated example, the tamper evident means 56 is in the form of a ring that is attached by frangible means or portions 60 to lower surface 48 of cap 40. However, other tamper evident means could be provided if required.

An inner surface of ring engages with the protruding ribs 58 on the neck section of bottle 4. On rotation of cap 40 relative to bottle 4, the inner surface of the ring remains in engagement with the protruding ribs 58 and the rotating force breaks frangible portions 60, thereby allowing release and separation of cap 40 from the tamper evident ring. Detachment of the tamper evident ring from cap 40 allows a user to determine whether the cap 40 has previously been opened.

In the illustrated example, a powdered composition is typically contained in bottle 4. The level of the composition contained in bottle 4 is typically below second end 16 of channel member 12. This allows air and composition to pass easily through further apertures 32 in use without obstruction.

Figure 1B:
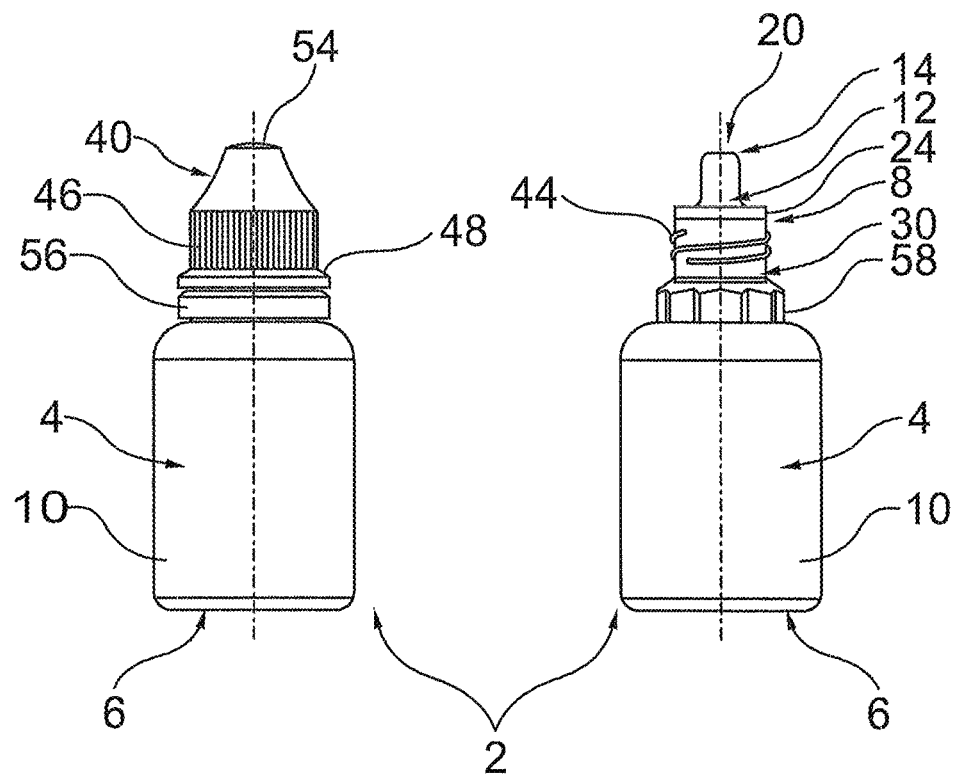

In use of the metered dose dispensing apparatus 2, the bottle 4 is normally located in an upright starting or storage position, as shown in FIGS. 1a and 1b. In this position, the base 6 of bottle 4 is located on a surface or is located below top surface 8. The composition contained within the bottle 4 is therefore resting on base 6 below channel member 12.

A user undertakes a priming action to fill recess 22 with composition. In order to do this, the user inverts bottle 4, such that base 6 is above top 8. The user may need to tap and/or shake the bottle a few times to move the composition from the bottle, through the further apertures 32 and into the channel member 12. The composition cannot exit the outlet aperture 20 because cap 40 is in place on bottle 4. The user then returns the bottle 4 to the starting, upright position and taps and/or shakes the same. This allows composition contained in the channel member to fall into recess 22, and excess composition that is not contained in recess 22 to pass out through further apertures 32 of channel member 12 and back into the bottle. The bottle is now primed with a metered dose of the composition. The user removes cap 40 from bottle 4 so that the bottle 4 is ready for use.

The user then locates the top end 14 of the channel member 12 in or just below their nasal cavity and squeezes the side walls 10 of bottle 4 towards each other. This action pushes air contained in bottle 4 through further apertures 32. As air passes opening 38 of recess 22, it entrains composition located in recess 22 in the airflow and carries the composition along channel 18, out through outlet aperture 20 and into the nasal cavity. Thus, the metered close is typically delivered from the bottle with the bottle located in a substantially upright position, thereby increasing the ease with which delivery of a composition can be made into a cavity, such as the nasal cavity.

As described in the applicant's previous patent, if the powdered composition contains HPMC, this powder forms a gel like substance on contact with moisture in the mucosa of the nasal cavity.

The dispensing apparatus of the present invention provides accurate and reproducible dispensing of a metered dose. This is illustrated in the table shown in FIG. 4. Ten 15 ml bottles (labelled 1-10) were partially filled with a powdered composition containing a mixture of HPMC and mint. The recess 22 in the channel member 12 was arranged so as to contain a metered dose of 800 mg of the powdered composition. The weight of each bottle with its powdered content was measured and recorded in column 2. The number of metered dosages contained in each bottle was recorded in column 3. The weight of the bottle with its powdered content was measured after a dispensing action and was recorded in column 4. This allowed the weight of the metered dose delivered during the dispensing action to be calculated, as shown in column 5. The % accuracy of the dose delivered as a measure of average weight of powder delivered is shown in column 6. It can be seen than the average % accuracy is 0.004, thereby providing sufficient accuracy in metered dose to prevent over dosing or under dosing with the composition.

An alternative embodiment of the channel member 12 is shown in FIGS. 5a-5c. In this embodiment the second end 16 is not a blind end as with the previous embodiment but is provided with the further apertures 32 surrounding the recess 22. The recess 22 is supported substantially centrally of hollow channel 18 via support arms 100 just above second end 16. As such, excess composition not contained in recess 22 falls out through second end 16 through further apertures 32.

It will be appreciated by persons skilled in the art that the dimensions of the recess can be changed to allow different dosages of composition to be contained therein, thereby changing the metered dose that can be delivered via the apparatus.

The further apertures are arranged on the channel member such that they do not interfere with the engagement of the channel member with the neck of the bottle and allow excess composition that is not contained within the recess of the channel member to move into and out of the channel member.

The metered dose apparatus of the present invention could be used with any other suitable composition dispensing apparatus, such as for example a liquid dropper and/or the like.

The invention claimed is:

1. A metered dose dispensing apparatus for delivering and/or dispensing a pre-determined amount of a powder, said dispensing apparatus including
a dispensing mechanism in the form of a channel member having a single integral linear hollow channel connecting a first end and a second opposite blind end, the single integral linear hollow channel having two or more inlets a spaced distance from the second opposite blind end for allowing powder to enter the single integral hollow channel,
an outlet at the first end of the single integral linear hollow channel for allowing powder containable within the single integral linear hollow channel to be dispensed therefrom during a dispensing action of the dispensing apparatus,
the single integral linear hollow channel provided between the two or more inlets and the outlet for allowing powder to move between the two or more inlets and the outlet,
and wherein the two or more inlets are located at the same height and/or distance from the first end and/or the second opposite blind end of the single integral linear hollow channel;
and wherein the second opposite blind end forms a recess beneath and connecting to the single integral linear hollow channel, dimensions of the recess defining or substantially defining the pre-determined amount of powder that can be delivered through the outlet aperture for each dispensing action of the dispensing apparatus, and wherein the two or more inlets defined in the dispensing mechanism are arranged and/or is of such dimensions that excess powder contained in the single integral linear hollow channel that cannot fit into the recess is able to pass through said inlets and out of the single integral linear hollow channel in use prior to a dispensing of product from the outlet, and
a deformable container in which the dispensing mechanism is located, the dispensing apparatus arranged such that deformation of the container as a result of one or more sides of the container being squeezed in use allows a volume of air or gas containable within the container to be propelled through the two or more inlets, single integral linear hollow channel and outlet and as the propelled air passes the recess in the single integral linear hollow channel, any powder contained within the recess is carried out through the outlet.

2. The dispensing apparatus according to claim 1 wherein the two or more inlets are defined in the single integral linear hollow channel a pre-determined spaced distance apart from the recess.

3. The dispensing apparatus according to claim 1 wherein the outlet is provided at or adjacent a first end of the single integral linear hollow channel, and the two or more inlets are provided at a second end of the single integral linear hollow channel and/or at an end opposite to an end in which the outlet is defined.

4. The dispensing apparatus according to claim 1 wherein the inlets and/or the walls defining the two or more inlets have a narrowing taper from an external wall of the single integral linear hollow channel to an internal wall of the single integral linear hollow channel and/or vice versa, or are linear or substantially linear in form from the external wall of the single integral linear hollow channel to the internal wall of the single integral linear hollow channel.

5. The dispensing apparatus according to claim 1 wherein the dispensing mechanism and/or single integral linear hollow channel are located in and fitted to a bottle, container or reservoir by friction fit, interference fit, snap fit, attachment, screw thread arrangement, protrusion/recess arrangement, snap fit connection, welding, adhesive or inter-engaging members.

6. The dispensing apparatus according to claim 1 wherein a cap, lid or closure is provided over the outlet of the dispensing mechanism and/or single integral linear hollow channel when in a bottle, container or reservoir when the dispensing apparatus is not in use or during a priming operation of the dispensing apparatus.

7. The dispensing apparatus according to claim 6 wherein a pin or protrusion member defined on an interior surface of the cap, lid or closure protrudes in the outlet of the single integral linear hollow channel to prevent composition from exiting the single integral linear hollow channel.

8. A method of using a dispensing apparatus for delivering and/or dispensing a pre-determined amount of a powder, said dispensing apparatus including a dispensing mechanism having two or more inlets for allowing powder to enter the dispensing mechanism, an outlet for allowing powder containable within the dispensing mechanism to be dispensed therefrom during a dispensing action of the dispensing apparatus, and a single integral hollow linear channel connecting the two or more inlets and the outlet for allowing powder to move linearly between the two or more inlets and the outlet, said channel having first and second ends, and wherein said method includes the steps of moving powder through the two or more inlets and into the single integral hollow linear channel of the dispensing mechanism, allowing powder contained within the single integral hollow linear channel to move into a recess beneath and connecting to the single integral hollow linear channel, dimensions of the recess defining or substantially defining the pre-determined amount of product that can be delivered through the outlet for each dispensing action of the dispensing apparatus, allowing excess powder contained in the single integral hollow linear channel that cannot fit into the recess to move through the inlets and out of the single integral hollow linear channel prior to dispensing powder contained within the recess from the outlet, deforming the apparatus by squeezing one or more side walls of the apparatus, propelling a volume of air or gas contained within the apparatus through the two or more inlets, single integral hollow linear channel, and outlet and carrying any powder contained within the recess in the propelled air through the outlet to provide dispensing, wherein the two or more inlets are located at the same height and/or distance from the first and/or second ends of the single integral hollow linear channel.

9. A method according to claim 8 wherein the dispensing mechanism is located in a bottle, container or reservoir in use, said bottle, container or reservoir is inverted prior to a dispensing action to allow product contained within the bottle, container or reservoir to pass through the inlets and into the single integral hollow linear channel of the dispensing mechanism, and wherein the bottle, container or reservoir is returned to an upright or starting position after inverting so as to allow product contained within the single integral hollow linear channel to fall into the recess prior to a dispensing action.

10. A method of using a dispensing apparatus for delivering and/or dispensing a pre-determined amount of a powder, said dispensing apparatus including dispensing mechanism having two or more inlets for allowing powder to enter the dispensing mechanism, an outlet for allowing powder containable within the dispensing mechanism to be dispensed therefrom during a dispensing action of the dispensing apparatus, and a single integral hollow linear channel provided between the two or more inlets and the outlet for allowing powder to move linearly between the two or more inlets and the outlet, said channel having first and second ends, and wherein said method includes the steps of: inverting the apparatus from an upright position to cause powder to move through the two or more inlets and into the single integral hollow linear channel of the dispensing mechanism, returning the apparatus to the upright position to allow powder contained within the single integral hollow linear channel to move into a recess beneath and connecting to the single integral hollow linear channel, dimensions of the recess defining or substantially defining the pre-determined amount of product that can be delivered through the outlet for each dispensing action of the dispensing apparatus, allowing excess powder contained in the single integral hollow linear channel that cannot fit into the recess to move through the two or more inlets and out of the single integral hollow linear channel prior to dispensing powder contained within the recess from the outlet, deforming the apparatus by squeezing one or more side walls of the apparatus, propelling a volume of air or gas contained within the apparatus through the two or more inlets, single integral hollow linear channel, and outlet and carrying any powder contained within the recess in the propelled air through the outlet to provide dispensing, wherein the two or more inlets are located at the same height and/or distance from the first and/or second ends of the single integral hollow linear channel.

\* \* \* \* \*